(12) United States Patent
Hoskonen et al.

(10) Patent No.: US 7,496,400 B2
(45) Date of Patent: Feb. 24, 2009

(54) SENSOR ARRANGEMENT

(75) Inventors: Terho Hoskonen, Järvenpää (FI); Lasse Kamppari, Helsinki (FI); Minna Kymäläinen, Helsinki (FI); Magnus Kåll, Espoo (FI); Leena Pesu, Helsinki (FI)

(73) Assignee: GE Healthcare Finland Oy (FI)

( * ) Notice: Subject to any disclaimer, the term of this patent is extended or adjusted under 35 U.S.C. 154(b) by 435 days.

(21) Appl. No.: 10/688,863

(22) Filed: Oct. 17, 2003

(65) Prior Publication Data

US 2005/0085741 A1    Apr. 21, 2005

(51) Int. Cl.
*A61B 5/00*    (2006.01)
*A61B 5/04*    (2006.01)

(52) U.S. Cl. .................. 600/544; 600/300; 600/546

(58) Field of Classification Search .......... None
See application file for complete search history.

(56) References Cited

U.S. PATENT DOCUMENTS

| | | | |
|---|---|---|---|
| 4,595,013 A | | 6/1986 | Callahan et al. |
| 4,595,018 A | | 6/1986 | Rantala |
| 5,772,591 A | * | 6/1998 | Cram .................. 600/383 |
| 6,083,156 A | * | 7/2000 | Lisiecki .................. 600/301 |
| 6,233,472 B1 | * | 5/2001 | Bennett et al. .......... 600/383 |
| 6,389,312 B1 | * | 5/2002 | Duckert .................. 600/546 |
| 6,394,953 B1 | * | 5/2002 | Devlin et al. .......... 600/383 |
| 6,934,570 B2 | * | 8/2005 | Kiani et al. .......... 600/324 |
| 6,950,698 B2 | * | 9/2005 | Sarkela et al. .......... 600/544 |
| 2003/0009096 A1 | | 1/2003 | Lahteenmaki |
| 2004/0163648 A1 | * | 8/2004 | Burton .................. 128/204.21 |

FOREIGN PATENT DOCUMENTS

| | | |
|---|---|---|
| WO | 02/32305 | 4/2002 |
| WO | WO-03/057030 | 7/2003 |

OTHER PUBLICATIONS

*Chemical Biosensors*, Robert A. Peura, John G. Webster (ed.), Medical Instrumentation: Application and Design, New York: Wiley, 1998, pp. 469-472.
*A Practical Guide to Monitoring: Neuromuscular Function*, Sorin J. Brull et al., Datex-Ohmeda, 2002.
*Comparison of Neuromuscular Blockade in Upper Facial and Hypothenar Muscles*, Markku P. J. Paloheimo et al., Journal of Clinical Monitoring, vol. 4, No. 4, Little Brown and Company, 1988, pp. 256-260.
*Monitoring in Anesthesia and Critical Care Medicine*, Casey D. Blitt, Churchill Livingstone, 1985, pp. 326-327.

* cited by examiner

*Primary Examiner*—Robert L Nasser
(74) *Attorney, Agent, or Firm*—Andrus, Sceales, Starke & Sawall, LLP (57) ABSTRACT

Sensor arrangement for measuring anesthesia parameters from the head of a patient the sensor arrangement comprising a base element and an array of electrodes and an optical sensor for monitoring substances in tissues. In the sensor arrangement all electrodes and sensors are connected to a single connector or a series of connectors attached to the base element for connecting the sensor arrangement to a patient monitor.

17 Claims, 11 Drawing Sheets

The first embodiment.

SENSOR ARRANGEMENT

The present invention relates to measuring anesthesia parameters from the head of a patient.

The parameters widely used in anesthesia are Entropy, which is derived from EEG and FEMG signals, and NMT and SpO2. Currently the Entropy parameter is the only parameter, which is exclusively measured from the head of the patient. SpO2 is sometimes measured from the ear if extremities cannot be used. So far NMT is mainly monitored from the hand. The parameters mentioned above can be described shortly as follows.

SpO2 or pulse oximetry measures the oxygenation of the blood noninvasively. Blood absorbs red and infrared light differently depending on the oxygenation, ie. the colour of the blood varies with its oxygenation. By emitting red and infrared light through tissue and measuring the absorption of the two different wavelengths (red, about 660 nm and infrared, about 940 nm) the blood oxygenation can be calculated. There are two ways of doing this, transmission oximetry or reflectance oximetry. In transmission oximetry the emitter (two LEDs) and receiver (photodetector) are placed facing each other typically on each side of a finger, toe or earlobe. In reflectance oximetry the light is reflected below the tissue (eg. Chest, forehead or limbs) back to the same surface as the emitter. This way both the emitter and receiver can be placed on the same skin surface. These matters are described in "Chemical Biosensors", Peura, R. A., Webster J. G. (ed.), Medical Instrumentation: Application and Design. New York: Wiley, 1998, pp.469-472.

Neuro Muscular Transmission (NMT) is the transfer of an impulse between a nerve and a muscle in the neuromuscular junction. NMT can be blocked by neuromuscular blocking agents-drugs, which cause transient muscle paralysis and prevent the patient from moving and breathing spontaneously. Muscle relaxation is used during general anesthesia to enable endotracheal intubation and to provide the surgeon with optimal working conditions. The level of neuromuscular block is routinely measured by stimulating a peripheral nerve, usually in the hand, and by evaluating the muscle response. The muscle response can be measured either visually, by touching the hand, using a mechanical piezoelectric sensor or measuring the EMG response (ie. electrical muscle activity). These matters are described in "A Practical Guide to Monitoring: Neuromuscular Function", Sorin J. Brull et al, Datex-Ohmeda, 2002.

Neuromuscular transmission can also be measured from the face of the patient by stimulating the facial nerve and observing the response of the facial muscles. These matters are described in the article "Comparison of Neuromuscular Blockade in Upper Facial and Hypothenar Muscles", Paloheimo Markku P. J. et al, Journal of Clinical Monitoring, Vol 4, No 4, Little, Brown and Company, October 1988.

The entropy parameter is used to determine the level of hypnosis of an anesthesized patient. The Entropy parameter is based on EEG and EMG signals measured from the forehead of the patient. The EEG signal represents brain activity whereas EMG represents muscle activity. Entropy could be described as the level of irregularity in the EEG and EMG signals. When the patient is awake, there is more brain and muscle activity whereas an anesthesized patient has less brain and muscle activity. These matter are described in the PCT-document WO 02/32305 A1.

A considerable problem in the operating rooms is the large amount of cables and hoses extending from the patient to a patient monitor and other devices connected to the patient. The amount of cables and hoses is due to the fact that traditionally separate sensors have been connected for example to a patient monitor using a cable of its own or a hose of its own. This principle leads to a considerable amount of cables and hoses, which may cause difficulties in the operating rooms particularly in extreme situations.

The object of the invention is to provide a sensor arrangement by which the problems of the prior art technique can be eliminated. This is obtained by the invention. The basic idea of the invention is that all electrodes and sensors are connected to a single connector or alternatively to a series of connectors for connecting the sensor arrangement to a patient monitor.

The sensor described herein provides a combination of the basic adequacy of anesthesia parameters into one compact sensor. The sensor gives a significant improvement to the current level of ergonomics and usability. When using the invention the user only has to attach one sensor instead of three separate sensors, Entropy, NMT and SpO2. In addition all parameters are measured from the same area, the face of the patient. There is no need to attach any sensors on the hands of the patient, which would typically be the case for NMT and SpO2. The user also only needs to connect one cable to the sensor since all parameters are connected through one connector. Depending on the sensor design, it might be necessary to use separate connectors for some of the parameters to meet patient leakage current and isolation requirements.

As told above a considerable problem in the operating rooms using the prior art technique is the large amount of cables and hoses extending from the patient to the patient monitor and other devices connected to the patient. The present invention eliminates or at lest drastically reduces said problem by combining several parameters into one cable and thereby reducing the "cable clutter".

Currently the Entropy parameter is the only parameter, which is exclusively measured from the head of the patient. SpO2 is sometimes measured from the ear if extremities cannot be used. So far NMT is mainly monitored from hand, but in fact the face offers a good alternative location for NMT measurement. Since Entropy can also be measured from the forehead of the patient, the head is a logical location for the combined sensor. The Entropy electrodes are located on the forehead and temple area.

Electrodes are also used for NMT stimulus and can also be used for NMT measurement (muscle response is measured by measuring the EMG response). To reduce the number of electrodes needed, some of the Entropy and NMT electrodes can be shared between the two parameters. The measurements can then be multiplexed to stimulate and measure potentials for the two different parameters. NMT can be measured either using a mechanical sensor sensing physical muscle movement or using electrodes measuring muscle activity electrically (EMG). Using a mechanical sensor requires a separate piezo-electric sensor over the muscle where the response is to be measured.

SpO2 is typically measured from the extremities or from the ear. It is, however, possible to measure SpO2 anywhere on the body where you can place an optical emitter and detector in such a fashion that the emitted light passes through oxygenated tissue. On the head of the patient such areas are the ears and the nose, and if the light is reflected off the scull, the forehead can be used as well.

All parameters in the combined adequacy of anesthesia sensor can be reliably recorded from the head of the patient enabling a compact sensor. It is also possible to evaluate the amount of pain experienced by the patient (analgesia) by monitoring the heartrate and the amplitude of the plethysmographic curve (signal obtained from the SpO2 sensor). The analgesia parameter could also be derived from the SpO2 signal without additional sensors.

In the following the invention will be described in greater detail by means of the examples shown in the drawings enclosed. The FIGS. 1-11 describe eleven different embodiments of the invention.

Figure 1:
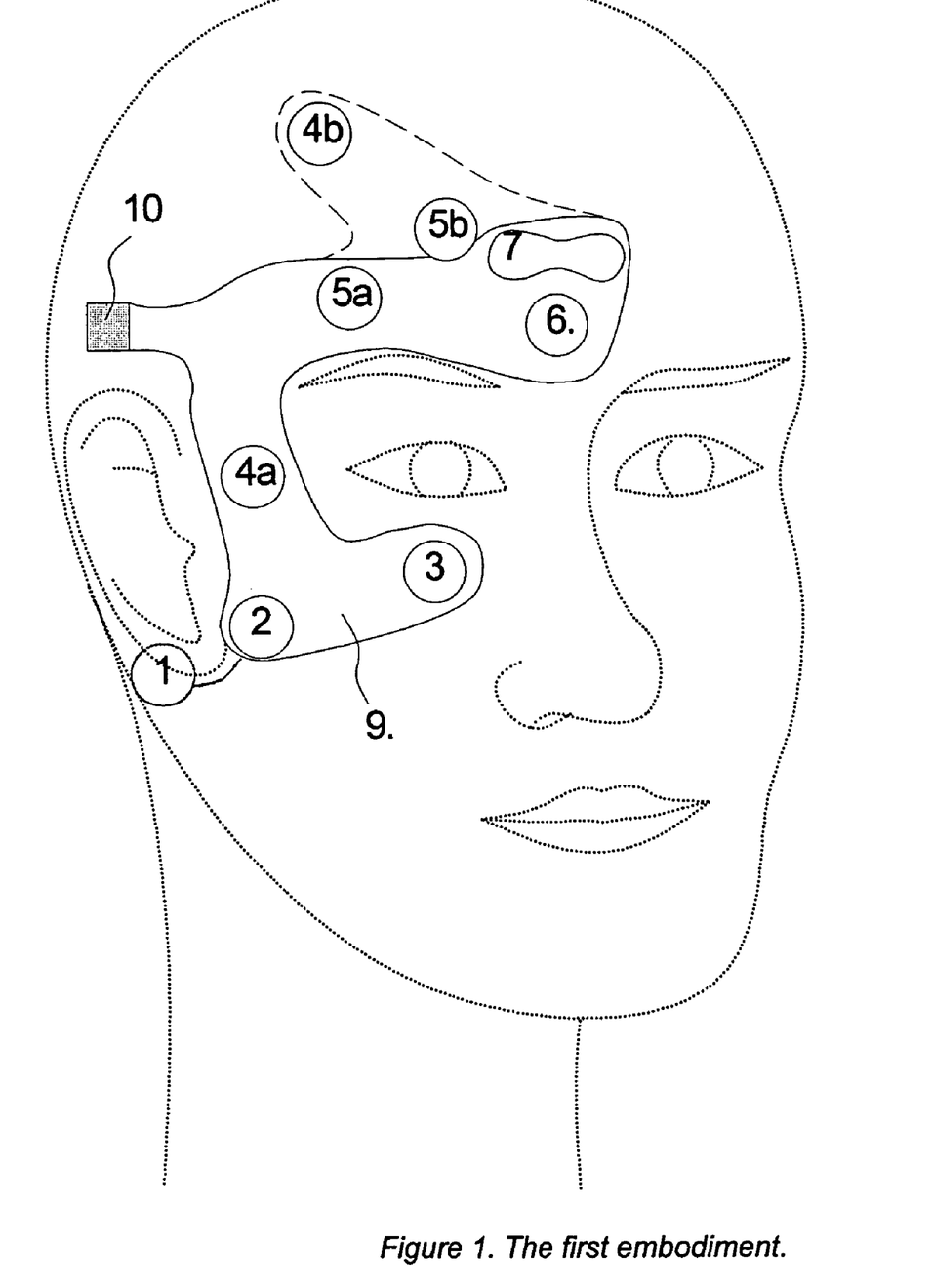
Figure 1. The first embodiment.

The first embodiment of the invention is described in FIG. 1. The sensor arrangement shown in FIG. 1 comprises an array of electrodes for measuring EEG, EMG and NMT. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. If location b is used, electrode 4a is also used. Electrode 4a is located on the temple area between the corner of the eye and the hairline. Electrode 5a is located above the eye at the same level as electrode 6, which is located between the eyebrows of the patient at the center of the forehead, approximately 4 cm above the nose. Electrode 4b is located at either location F3 or F4 (left or right side) of the International 10-20 system. The International 10-20 system is described in "Monitoring in Anesthesia and Critical Care Medicine", Casey D. Blitt, Churchill Livingstone, 1985. Electrode 5b is located between electrode 4b and electrode 6.

It is very advantageous to place electrode 5b essentially in the middle of electrodes 4b and 6 so that the distances between electrode 5b and electrode 4b, and electrode 5b and electrode 6 are essentially the same. In addition to these electrodes, a reflective optical sensor 7 for monitoring substances in tissues, e.g. SpO2 is placed on the face of the patient, anywhere where suitable for the structure of the sensor, eg. but not limited to on the forehead above electrode 6. The optical sensor 7 comprises an emitter and a receiver located close to each other. The emitter comprises LEDs of different wavelengths and the receiver comprises a photodetector.

Electrodes 1 and 2 are the NMT stimulus electrodes, stimulating the facial nerve. Electrodes 4a and 6 are the NMT recording electrodes and electrode 5(a or b) is the NMT grounding electrode. Electrodes 4(a or b) and 6 also record EEG and EMG signals used e.g. to derive the Entropy parameter. Electrode 5(a or b) is the reference electrode for the EEG and EMG measurement. The EEG and EMG measurement can be enhanced using electrode 3 e.g. but not limited to record eye movements. The EEG and EMG measurement can be done with or without electrode 3. The optical sensor measures e.g. the plethysmographic curve, the heartrate and the blood oxygen saturation.

The embodiment shown in FIG. 1 comprises also a base element 9. The base element 9 can be made of any appropriate flexible material, for example of plastic material. The electrodes and sensors described above can be attached to the base element by using any appropriate method known per se.

All electrodes and sensors described above are connected to a single connector 10 attached to the base element 9 as shown in FIG. 1. Instead of a single connector 10 a series of connectors may be used as told before.

Figure 2:
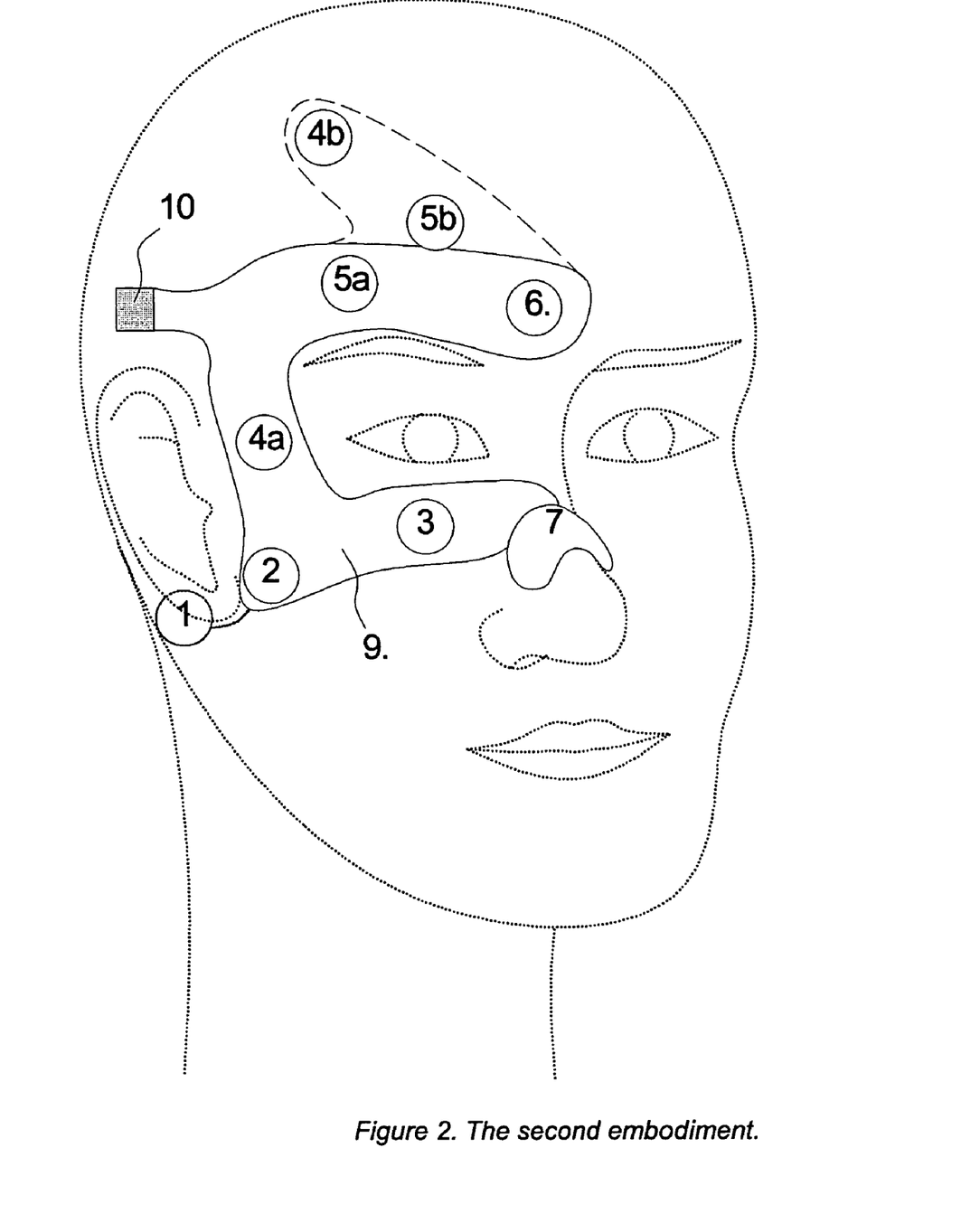
Figure 2. The second embodiment.

The second embodiment is described in FIG. 2. The sensor arrangement shown in FIG. 2 comprises an array of electrodes for measuring EEG, EMG and NMT. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. If location between the corner of the eye and the hairline. Electrode 5a is located above the eye at the same level as electrode 6, which is located between the eyebrows of the patient at the center of the forehead, approximately 4 cm above the nose. Electrode 4b is located at either location F3 or F4 (left or right side) of the International 10-20 system. Electrode 5b is located between electrode 4b and electrode 6.

It is very advantageous to place electrode 5b essentially in the middle of electrodes 4b and 6 so that the distances between electrode 5b and electrode 4b, and electrode 5b and electrode 6 are essentially the same. In addition to these electrodes, a transmission optical sensor 7 for monitoring substances in tissues, e.g. SpO2 is placed on the nose of the patient. The optical sensor 7 comprises an emitter and a receiver located on opposite sides of the nose. The emitter comprises LEDs of different wavelengths and the receiver comprises of a photodetector.

Electrodes 1 and 2 are the NMT stimulus electrodes, stimulating the facial nerve. Electrodes 4a and 6 are the NMT recording electrodes and electrode 5(a or b) is the NMT grounding electrode. Electrodes 4(a or b) and 6 also record EEG and EMG signals used e.g. to derive the Entropy parameter. Electrode 5(a or b) is the reference electrode for the EEG and EMG measurement. The EEG and EMG measurement can be enhanced using electrode 3 e.g. but not limited to record eye movements. The EEG and EMG measurement can be done with or without electrode 3. The optical sensor measures e.g. plethysmographic curve, the heartrate and the blood oxygen saturation.

The embodiment shown in FIG. 2 comprises also a base element 9. The base element 9 can be made of any appropriate flexible material, for example of plastic material. The electrodes and sensors described above can be attached to the base element by using any appropriate method known per se.

All electrodes and sensors described above are connected to a single connector 10 attached to the base element 9 as shown in FIG. 2. Instead of a single connector 10 a series of connectors may be used as told before.

Figure 3:
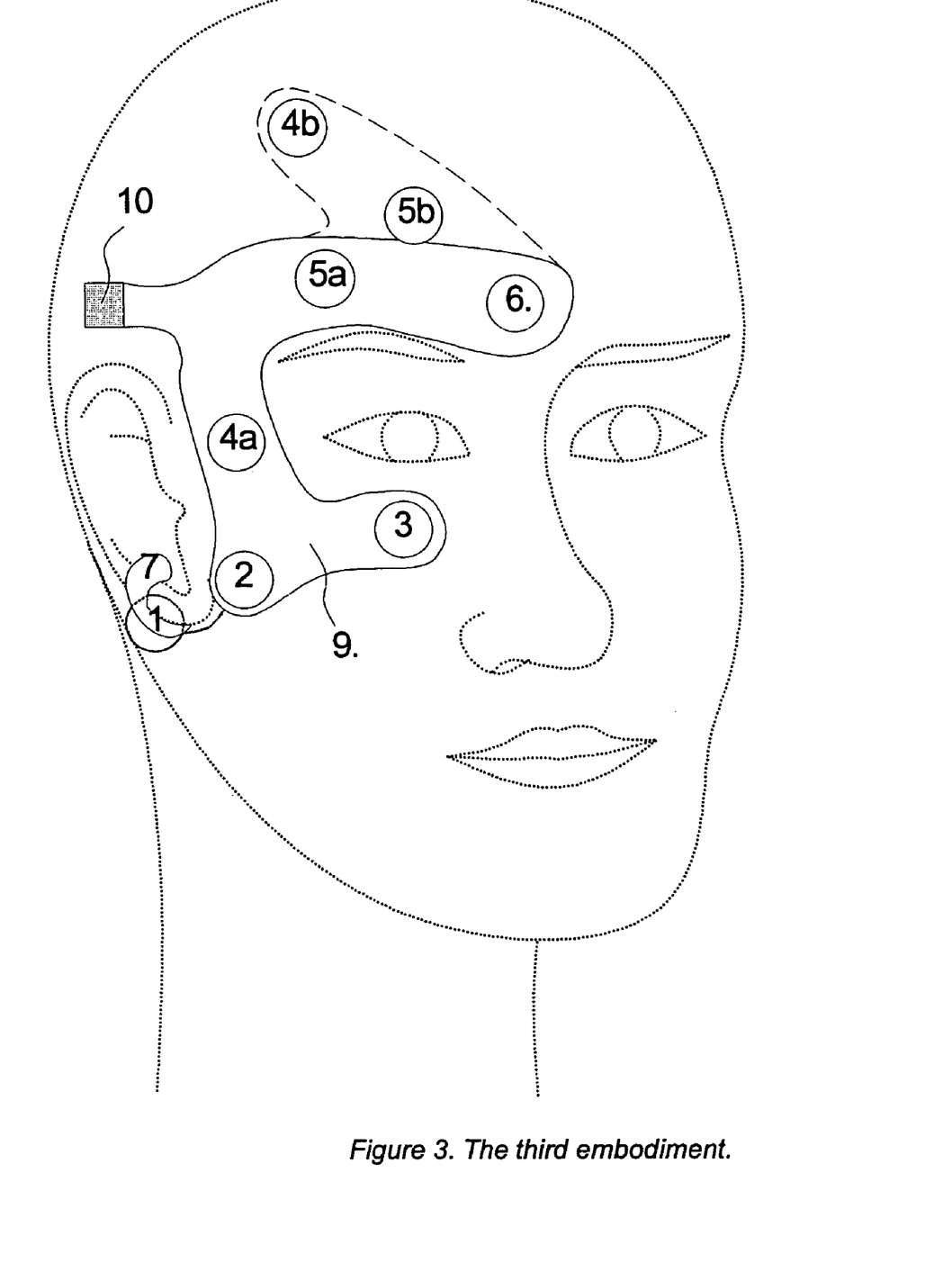
Figure 3. The third embodiment.

The third embodiment is described in FIG. 3. The sensor arrangement shown in FIG. 3 comprises an array of electrodes for measuring EEG, EMG and NMT. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. If location b is used, electrode 4a is also used. Electrode 4a is located on the temple area between the corner of the eye and the hairline. Electrode 5a is located above the eye at the same level as electrode 6, which is located between the eyebrows of the patient at the center of the forehead, approximately 4 cm above the nose. Electrode 4b is located at either location F3 or F4 (left or right side) of the International 10-20 system. Electrode 5b is located between electrode 4b and electrode 6.

It is very advantageous to place electrode 5b essentially in the middle of electrodes 4b and 6 so that the distances between electrode 5b and electrode 4b, and electrode 5b and electrode 6 are essentially the same. In addition to these electrodes, a transmission optical sensor 7 for monitoring substances in tissues, e.g. SpO2 is placed on the ear of the patient. The optical sensor 7 comprises an emitter and a receiver located on opposite sides of the auricle. The emitter comprises LEDs of different wavelengths and the receiver comprises a photodetector.

Electrodes 1 and 2 are the NMT stimulus electrodes, stimulating the facial nerve. Electrodes 4a and 6 are the NMT recording electrodes and electrode 5(a or b) is the NMT grounding electrode. Electrodes 4(a or b) and 6 also record EEG and EMG signals used e.g. to derive the Entropy parameter. Electrode 5(a or b) is the reference electrode for the EEG and EMG measurement. The EEG and EMG measurement can be enhanced using electrode 3 e.g. but not limited to record eye movements. The EEG and EMG measurement can be done with or without electrode 3. The optical sensor measures e.g. the plethysmographic curve, the heartrate and the blood oxygen saturation.

The embodiment shown in FIG. 3 comprises also a base element 9. The base element 9 can be made of any appropriate flexible material, for example of plastic material. The base element 9 can be formed and designed freely according to the existing need as shown in the Figures, ie. for example the base element 9 in FIG. 3 is slightly different when compared to the base element 9 in FIG. 1. The electrodes and sensors described above can be attached to the base element by using any appropriate method known per se.

All electrodes and sensors described above are connected to a single connector 10 attached to the base element 9 as shown in FIG. 3. Instead of a single connector 10 a series of connectors may be used as told before.

Figure 4:
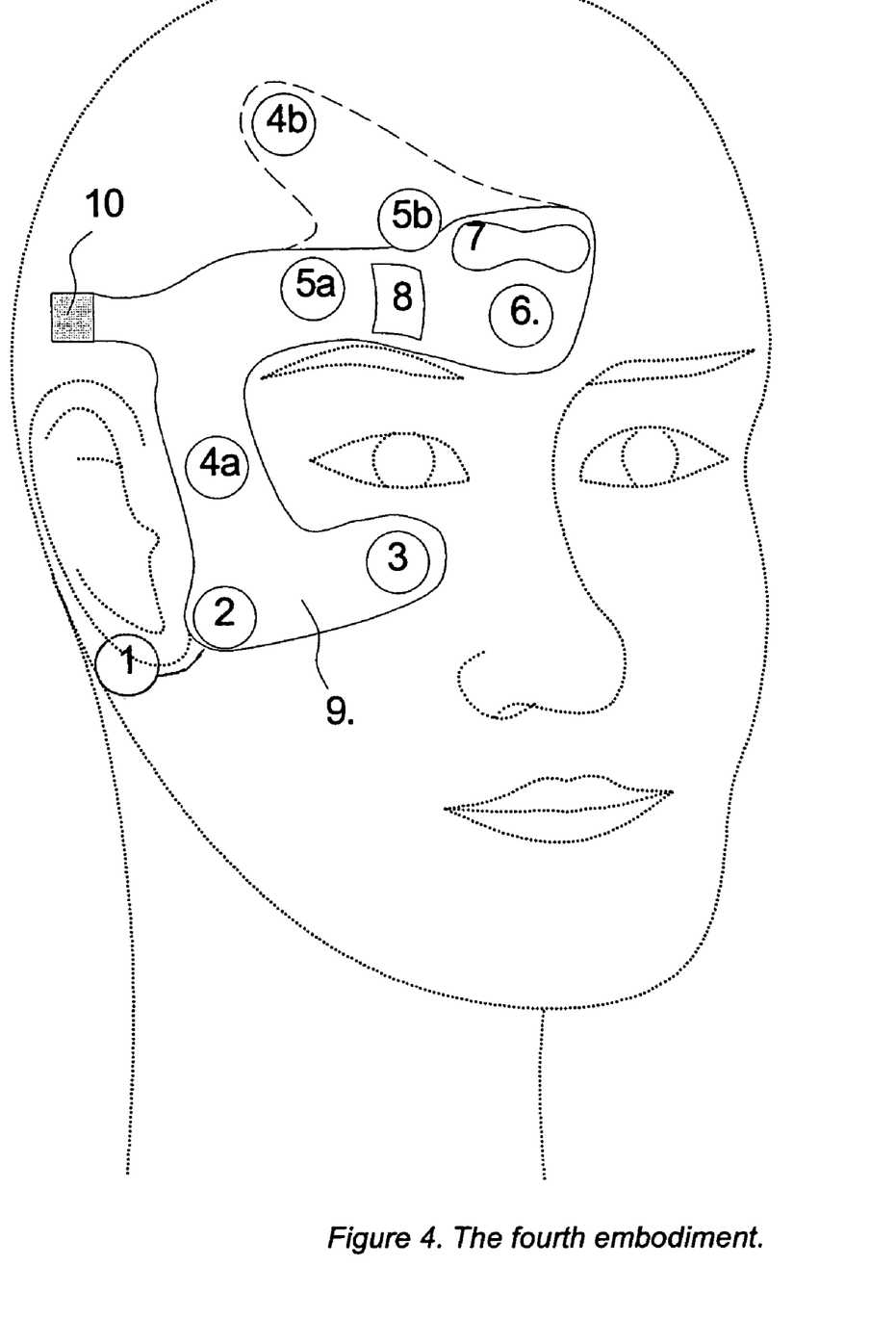
Figure 4. The fourth embodiment.

The fourth embodiment is described in FIG. 4. The sensor arrangement shown in FIG. 4 comprises an array of electrodes for measuring EEG, EMG and for NMT stimulus. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. Electrode 4a is located on the temple area between the corner of the eye and the hairline. Electrode 5a is located above the eye at the same level as electrode 6, which is located between the eyebrows of the patient at the center of the forehead, approximately 4 cm above the nose. Electrode 4b is located at either location F3 or F4 (left or right side) of the International 10-20 system. Electrode 5b is located between electrode 4b and electrode 6.

It is very advantageous to place electrode 5b essentially in the middle of electrodes 4b and 6 so that the distances between electrode 5b and electrode 4b, and electrode 5b and electrode 6 are essentially the same. In addition to these electrodes, a reflective optical sensor 7 for monitoring substances in tissues, e.g. SpO2 is placed on the face of the patient, anywhere where suitable for the structure of the sensor, eg. but not limited to on the forehead above electrode 6. The optical sensor 7 comprises an emitter and a receiver located close to each other. The emitter comprises LEDs of different wavelengths and the receiver comprises a photodetector. A mechanical piezoelectric sensor 8 is located over either the procerus, frontalis, corrugator or orbicularismuscle or a combination of these.

Electrodes 1 and 2 are the NMT stimulus electrodes, stimulating the facial nerve. Electrodes 4(a or b) and 6 record EEG and EMG signals used e.g. to derive the Entropy parameter. Electrode 5(a or b) is the reference electrode for the EEG and EMG measurement. The EEG and EMG measurement can be enhanced using electrode 3 e.g. but not limited to record eye movements. The EEG and EMG measurement can be done with or without electrode 3. The optical sensor measures e.g. the plethysmographic curve, the heartrate and the blood oxygen saturation. The mechanical piezoelectric sensor 8 records muscle response to NMT stimulus.

Also the embodiment shown in FIG. 4 comprises according to the invention a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In this embodiment all electrodes and sensors described above are connected to a single connector 10 attached to the base element 9 in the same way as described in FIGS. 1-3. Instead of a single connector 10 a series of connectors may be used as told before.

Figure 5:
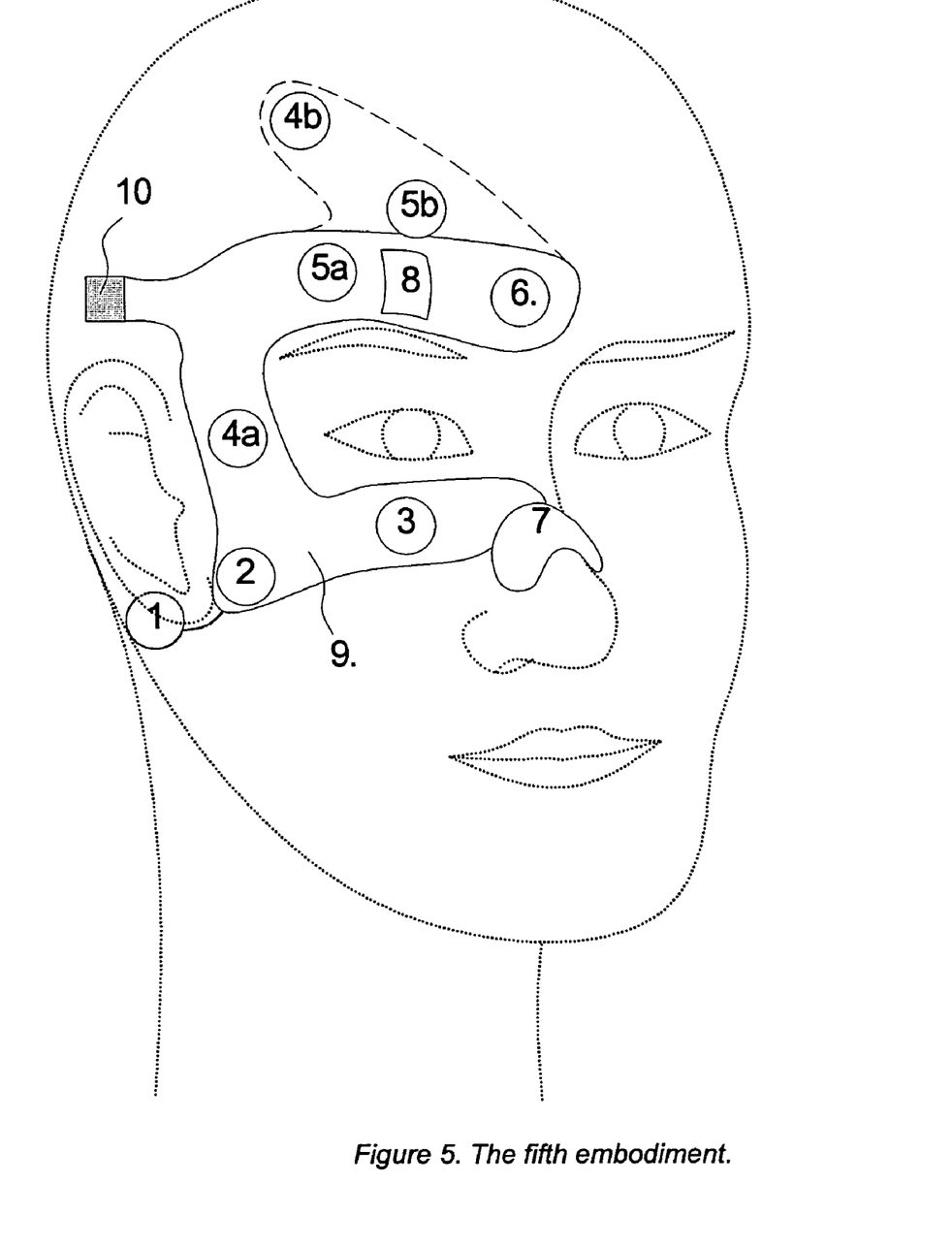
Figure 5. The fifth embodiment.

The fifth embodiment is described in FIG. 5. The sensor arrangement shown in FIG. 5 comprises an array of electrodes for measuring EEG, EMG and for NMT stimulus. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. Electrode 4a is located on the temple area between the corner of the eye and the hairline. Electrode 5a is located above the eye at the same level as electrode 6, which is located between the eyebrows of the patient at the center of the forehead, approximately 4 cm above the nose. Electrode 4b is located at either location F3 or F4 (left or right side) of the International 10-20 system. Electrode 5b is located between electrode 4b and electrode 6.

It is very advantageous to place electrode 5b essentially in the middle of electrodes 4b and 6 so that the distances between electrode 5b and electrode 4b, and electrode 5b and electrode 6 are essentially the same. In addition to these electrodes, a transmission optical sensor 7 for monitoring substances in tissues, e.g. SpO2 is placed on the nose of the patient. The optical sensor 7 comprises an emitter and a receiver located on opposite sides of the nose. The emitter comprises LEDs of different wavelengths and the receiver comprises a photodetector. A mechanical piezoelectric sensor 8 is located over either the procerus, frontalis, corrugator or orbicularis muscle or a combination of these.

Electrodes 1 and 2 are the NMT stimulus electrodes, stimulating the facial nerve. Electrodes 4(a or b) and 6 record EEG and EMG signals used e.g. to derive the Entropy parameter. Electrode 5(a or b) is the reference electrode for the EEG and EMG measurement. The EEG and EMG measurement can be enhanced using electrode 3 e.g. but not limited to record eye movements. The EEG and EMG measurement can be done with or without electrode 3. The optical sensor measures e.g. the plethysmographic curve, the heartrate and the blood oxygen saturation. The mechanical piezoelectric sensor 8 records muscle response to NMT stimulus.

Also the embodiment shown in FIG. 5 comprises according to the invention a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In this embodiment all electrodes and sensors described above are connected to a single connector 10 attached to the base element 9 in the same way as described in FIGS. 1-4. Instead of a single connector 10 a series of connectors may be used as told before in connection with the previous embodiments.

Figure 6:
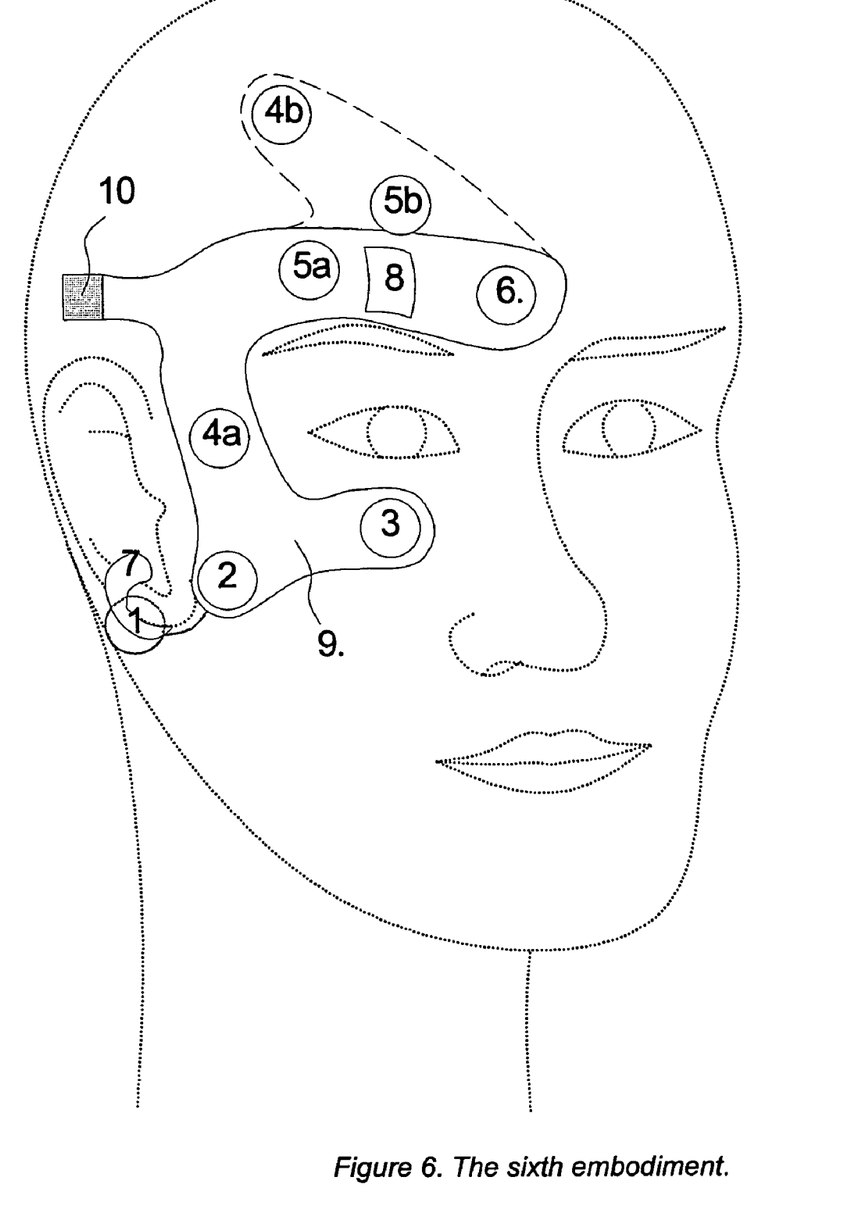
Figure 6. The sixth embodiment.

The sixth embodiment is described in FIG. 6. The sensor arrangement shown in FIG. 6 comprises an array of electrodes for measuring EEG, EMG and for NMT stimulus. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. Electrode 4a is located on the temple area between the corner of the eye and the hairline. Electrode 5a is located above the eye at the same level as electrode 6, which is located between the eyebrows of the patient at the center of the forehead, approximately 4 cm above the nose. Electrode 4*b* is located at either location F3 or F4 (left or right side) of the International 10-20 system. Electrode 5*b* is located between electrode 4*b* and electrode 6.

It is very advantageous to place electrode 5*b* essentially in the middle of electrodes 4*b* and 6 so that the distances between electrode 5*b* and electrode 4*b*, and electrode 5*b* and electrode 6 are essentially the same. In addition to these electrodes, a transmission optical sensor 7 for monitoring substances in tissues, e.g. SpO2 is placed on the ear of the patient. The optical sensor 7 comprises an emitter and a receiver located on opposite sides of either auricle. The emitter comprises LEDs of different wavelengths and the receiver comprises a photodetector. A mechanical piezoelectric sensor 8 is located over either the procerus, frontalis, corrugator or orbicularis muscle or a combination of these.

Electrodes 1 and 2 are the NMT stimulus electrodes, stimulating the facial nerve. Electrodes 4(*a* or *b*) and 6 record EEG and EMG signals used e.g. to derive the Entropy parameter. Electrode 5(*a* or *b*) is the reference electrode for the EEG and EMG measurement. The EEG and EMG measurement can be enhanced using electrode 3 e.g. but not limited to record eye movements. The EEG and EMG measurement can be done with or without electrode 3. The optical sensor measures e.g. the plethysmographic curve, the heartrate and the blood oxygen saturation. The mechanical piezoelectric sensor 8 records muscle response to NMT stimulus.

Also the embodiment shown in FIG. 6 comprises according to the invention a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In this embodiment all electrodes and sensors described above are connected to a single connector 10 attached to the base element 9 in the same way as described in FIGS. 1-5. Instead of a single connector 10 a series of connectors may be used as told before in connection with the embodiments shown in FIGS. 1-5.

Figure 7:
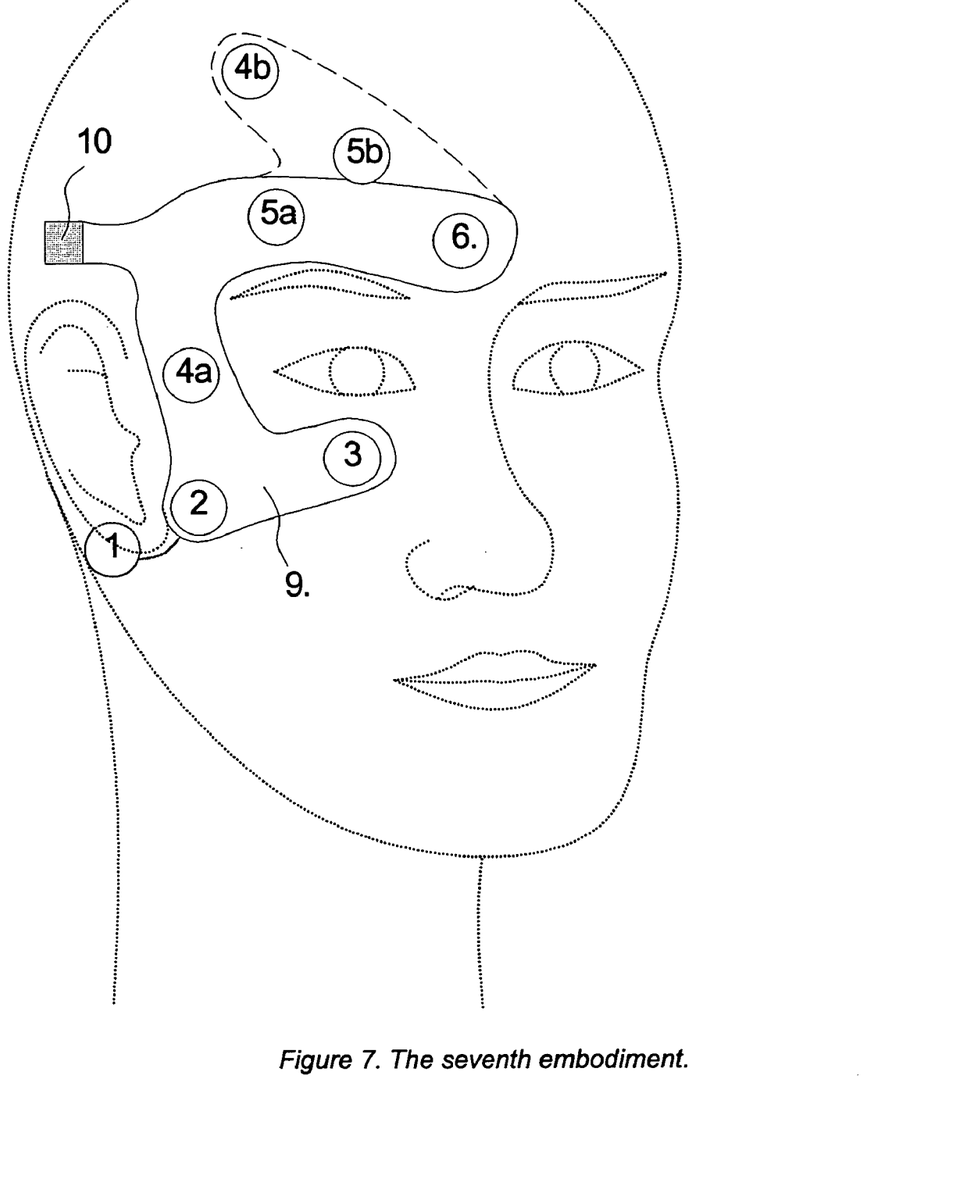
Figure 7. The seventh embodiment.

The seventh embodiment is described in FIG. 7. The sensor arrangement shown in FIG. 7 comprises an array of electrodes for measuring EEG, EMG and NMT. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. If location b is used, electrode 4*a* is also used. Electrode 4*a* is located on the temple area between the corner of the eye and the hairline. Electrode 5*a* is located above the eye at the same level as electrode 6, which is located between the eyebrows of the patient at the center of the forehead, approximately 4 cm above the nose. Electrode 4*b* is located at either location F3 or F4 (left or right side) of the International 10-20 system. Electrode 5*b* is located between electrode 4*b* and electrode 6.

It is very advantageous to place electrode 5*b* essentially in the middle of electrodes 4*b* and 6 so that the distances between electrode 5*b* and electrode 4*b*, and electrode 5*b* and electrode 6 are essentially the same.

Electrodes 1 and 2 are the NMT stimulus electrodes, stimulating the facial nerve. Electrodes 4*a* and 6 are the NMT recording electrodes and electrode 5(*a* or *b*) is the NMT grounding electrode. Electrodes 4(*a* or *b*) and 6 also record EEG and EMG signals used e.g. to derive the Entropy parameter. Electrode 5(*a* or *b*) is the reference electrode for the EEG and EMG measurement. The EEG and EMG measurement can be enhanced using electrode 3 e.g. but not limited to record eye movements. The EEG and EMG measurement can be done with or without electrode 3.

Also the embodiment shown in FIG. 7 comprises according to the invention a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In this embodiment all electrodes and sensors described above are connected to a single connector 10 attached to the base element 9 in the same way as described in FIGS. 1-6. Instead of a single connector 10 a series of connectors may be used as told before in connection with the embodiments shown in FIGS. 1-6.

Figure 8:
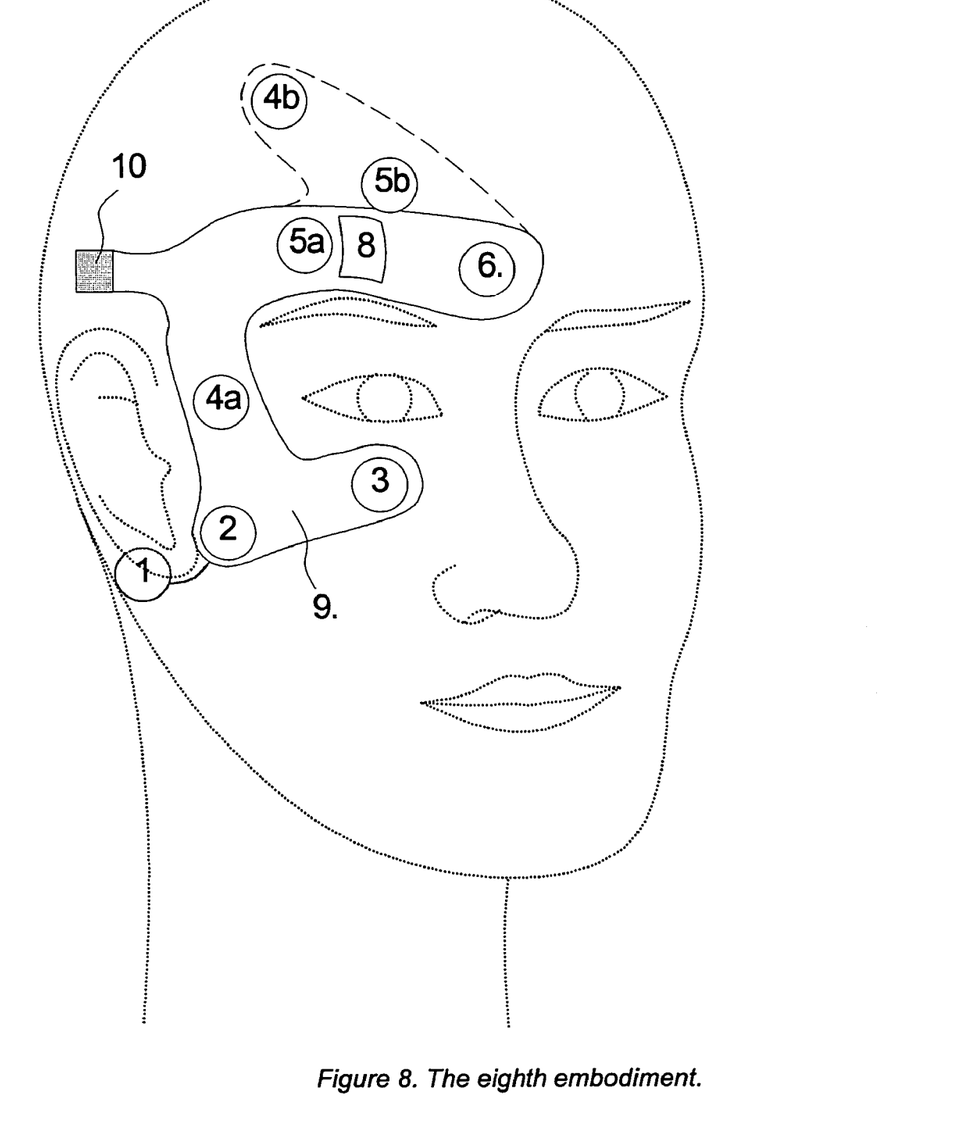
Figure 8. The eighth embodiment.

The eighth embodiment is described in FIG. 8. The sensor arrangement shown in FIG. 8 comprises an array of electrodes for measuring EEG, EMG and for NMT stimulus. The electrodes are located on the face of the patient. Electrode 1 is located just posterior to the lower part of the pinna and electrode 2 is located just anterior to the tragus. Electrode 3 is located below the eye. Electrodes 4 and 5 have two alternative locations, a and b. Electrode 4*a* is located on the temple area between the corner of the eye and the hairline. Electrode 5*a* is located above the eye at the same level as electrode 6, which is located between the eyebrows of the patient at the center of the forehead, approximately 4 cm above the nose. Electrode 4*b* is located at either location F3 or F4 (left or right side) of the International 10-20 system. Electrode 5*b* is located between electrode 4*b* and electrode 6.

It is very advantageous to place electrode 5*b* essentially in the middle of electrodes 4*b* and 6 so that the distances between electrode 5*b* and electrode 4*b*, and electrode 5*b* and electrode 6 are essentially the same. A mechanical piezoelectric sensor 8 is located over either the procerus, frontalis, corrugator or orbicularis muscle or a combination of these.

Electrodes 1 and 2 are the NMT stimulus electrodes, stimulating the facial nerve. Electrodes 4(*a* or *b*) and 6 record EEG and EMG signals used e.g. to derive the Entropy parameter. Electrode 5(*a* or *b*) is the reference electrode for the EEG and EMG measurements. The EEG and EMG measurement can be enhanced using electrode 3 e.g. but not limited to record eye movements. The EEG and EMG measurement can be done with or without electrode 3. The mechanical piezoelectric sensor 8 records muscle response to NMT stimulus.

Also the embodiment shown in FIG. 8 comprises according to the invention a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In this embodiment all electrodes and sensors described above are connected to a single connector 10 attached to the base element 9 in the same way as described in connection with FIGS. 1-7 instead of a single connector 10 a series of connectors may be used as told before in connection with the embodiments shown in FIGS. 1-7.

Figure 9:
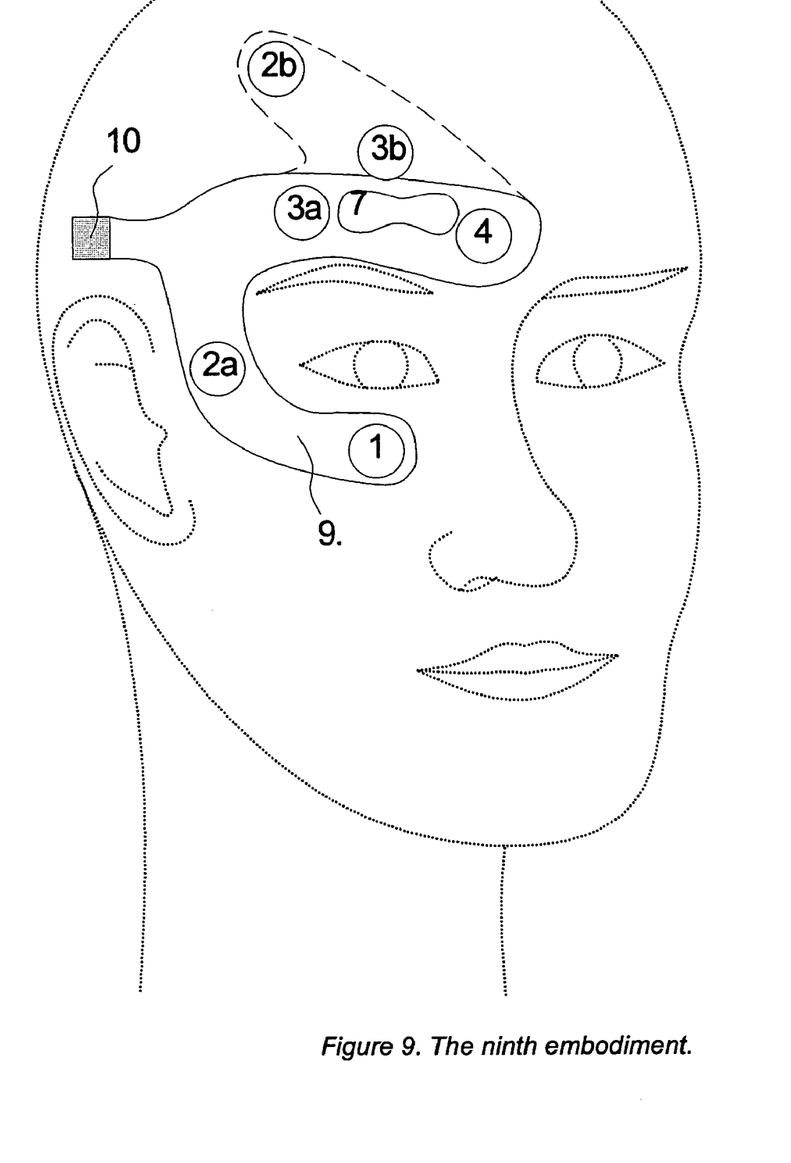
Figure 9. The ninth embodiment.

The ninth embodiment is described in FIG. 9. The sensor arrangement shown in FIG. 9 comprises an array of electrodes for measuring EEG and EMG. The electrodes are located on the face of the patient. Electrode 1 is located below the eye. Electrodes 2 and 3 have two alternative locations, a and b. Electrode 2a is located on the temple area between the corner of the eye and the hairline. Electrode 3a is located above the eye at the same level as electrode 4, which is located between the eyebrows of the patient at the center of the forehead, approximately 4 cm above the nose. Electrode 2b is located at either location F3 or F4 (left or right side) of the International 10-20 system. Electrode 3b is located between electrode 2b and electrode 4.

It is very advantageous to place electrode 3b essentially in the middle of electrodes 2b and 4 so that the distances between electrode 3b and electrode 2b, and electrode 3b and electrode 4 are essentially the same. In addition to these electrodes, a reflective optical sensor 7 for monitoring substances in tissues, e.g. SpO2 is placed on the face of the patient, anywhere where suitable for the structure of the sensor, for example on the forehead as shown in FIG. 9. The optical sensor 7 comprises an emitter and a receiver located close to each other. The emitter comprises LEDs of different wavelengths and the receiver comprises a photodetector.

Electrodes 2(*a* or *b*) and 4 record EEG and EMG signals used e.g. to derive the Entropy parameter. Electrode 3(*a* or *b*) is the reference electrode for the EEG and EMG measurement. The EEG and EMG measurement can be enhanced using electrode 1 e.g. but not limited to record eye movements. The EEG and EMG measurement can be done with or without electrode 1. The optical sensor measures e.g. the plethysmographic curve, the heartrate and the blood oxygen saturation.

The embodiment shown in FIG. 9 comprises also according to the invention a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In this embodiment all electrodes and sensors described above are connected to a single connector 10 attached to the base element 9 in the same way as described in connection with FIGS. 1-8. Instead of a single connector 10 a series of connectors may be used as told before in connection with the embodiments shown in FIGS. 1-8.

Figure 10:
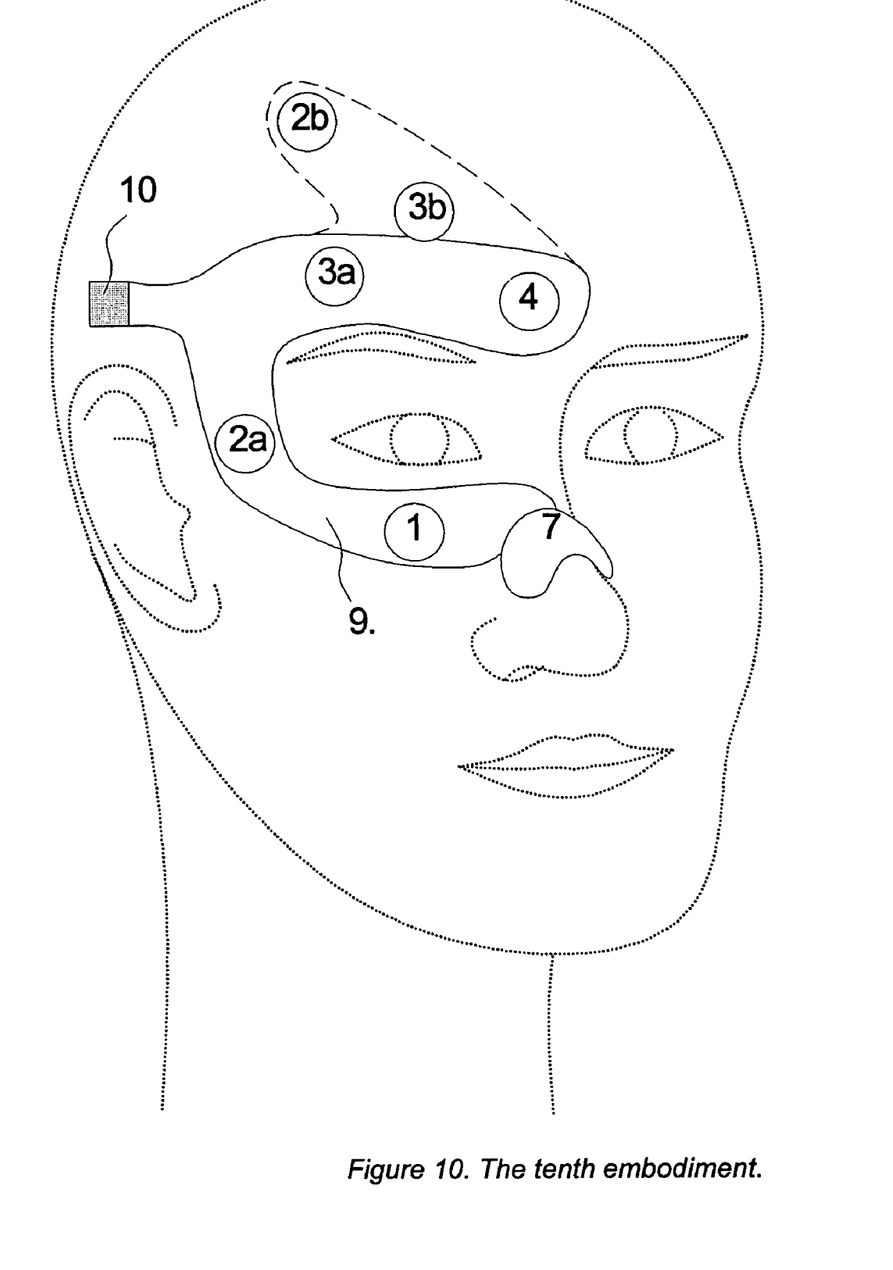
Figure 10. The tenth embodiment.

The tenth embodiment is described in FIG. 10. The sensor arrangement shown in FIG. 10 comprises an array of electrodes for measuring EEG and EMG. The electrodes are located on the face of the patient. Electrode 1 is located below the eye. Electrodes 2 and 3 have two alternative locations, a and b. Electrode 2a is located on the temple area between the corner of the eye and the hairline. Electrode 3a is located above the eye at the same level as electrode 4, which is located between the eyebrows of the patient at the center of the forehead, approximately 4 cm above the nose. Electrode 2b is located at either location F3 or F4 (left or right side) of the International 10-20 system. Electrode 3b is located between electrode 2b and electrode 4.

It is very advantageous to place electrode 3b essentially in the middle of electrodes 2b and 4 so that the distances between electrode 3b and electrode 2b, and electrode 3b and electrode 4 are essentially the same. In addition to these electrodes, a transmission optical sensor 7 for monitoring substances in tissues, e.g. SpO2 is placed on the nose of the patient. The optical sensor 7 comprises an emitter and a receiver located on opposite sides of the nose. The emitter comprises LEDs of different wavelengths and the receiver comprises a photodetector.

Electrodes 2(*a* or *b*) and 4 record EEG and EMG signals used e.g. to derive the Entropy parameter. Electrode 3(*a* or *b*) is the reference electrode for the EEG and EMG measurement. The EEG and EMG measurement can be enhanced using electrode 1 e.g. but not limited to record eye movements. The EEG and EMG measurement can be done with or without electrode 1. The optical sensor measures e.g. the plethysmographic curve, the heartrate and the blood oxygen saturation.

As told in connection with the previous embodiments also the embodiment shown in FIG. 10 comprises a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In the embodiment of FIG. 10 all electrodes and sensors described above are connected to a single connector 10 attached to the base element 9 in the same way as described in connection with FIGS. 1-9. Instead of a single connector 10 a series of connectors may be used as told before in connection with the embodiments shown in FIGS. 1-9.

Figure 11:
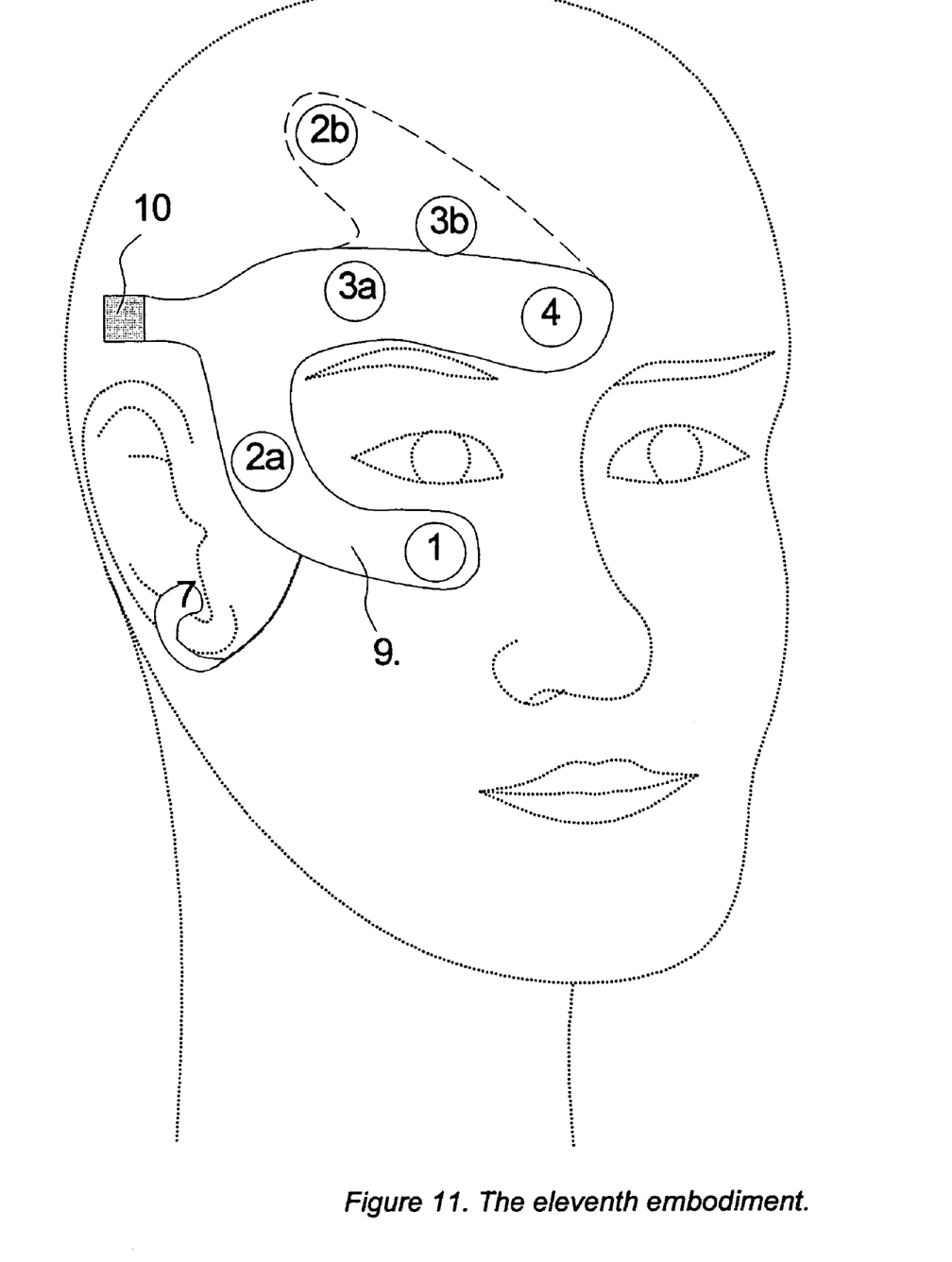
Figure 11. The eleventh embodiment.

The eleventh embodiment is described in FIG. 11. The sensor arrangement shown in FIG. 11 comprises an array of electrodes for measuring EEG and EMG. The electrodes are located on the face of the patient. Electrode 1 is located below the eye. Electrodes 2 and 3 have two alternative locations, a and b. Electrode 2a is located on the temple area between the corner of the eye and the hairline. Electrode 3a is located above the eye at the same level as electrode 4, which is located between the eyebrows of the patient at the center of the forehead, approximately 4 cm above the nose. Electrode 2b is located at either location F3 or F4 (left or right side) of the International 10-20 system. Electrode 3b is located between electrode 2b and electrode 4.

It is very advantageous to place electrode 3b essentially in the middle of electrodes 2b and 4 so that the distances between electrode 3b and electrode 2b, and electrode 3b and electrode 4 are essentially the same. In addition to these electrodes, a transmission optical sensor 7 for monitoring substances in tissues, e.g. SpO2 is placed on the ear of the patient. The optical sensor 7 comprises an emitter and a receiver located on opposite sides of either auricle. The emitter comprises LEDs of different wavelengths and the receiver comprises a photodetector.

Electrodes 2(*a* or *b*) and 4 record EEG and EMG signals used e.g. to derive the Entropy parameter. Electrode 3(*a* or *b*) is the reference electrode for the EEG and EMG measurement. The EEG and EMG measurement can be enhanced using electrode 1 e.g. but not limited to record eye movements. The EEG and EMG measurement can be done with or without electrode 1. The optical sensor measures e.g. the plethysmographic curve, the heartrate and the blood oxygen saturation.

As told in connection with the previous embodiments also the embodiment shown in FIG. 11 comprises a base element 9. The base element 9 can be made of any appropriate flexible material, for example of plastic material. The electrodes and sensors described above can be attached to the base element by using any appropriate method known per se. As told before the form and the structure of the base element can be designed quite freely according to the existing need.

In the embodiment of FIG. 11 all electrodes and sensors described above are connected to a single connector 10 attached to the base element 9 in the same way as described in connection with FIGS. 1-10. Instead of a single connector 10 a series of connectors may be used as told before in connection with the embodiments shown in FIGS. 1-10.

In the embodiments shown in FIGS. 1-11 all electrodes and sensors are connected to a single connector 10 for connecting the sensor arrangement to a patient monitor. Said arrangement reduces the amount of cables needed between the patient and the patient monitor. As told above depending on the sensor design it might however be necessary to use separate connectors for some of the parameters, ie. for some of the electrodes used, to meet patient leakage current and isolation requirements. Said separate connectors can be arranged as a compact unit, in which the connectors are placed side by side for example.

The above embodiments of the invention are by no means intended to limit the invention, but the invention can be modified quite freely within the scope of the claims. Accordingly, it is clear that an embodiment of the invention or its details do not necessarily need to be just as described in the figures, but solutions of other kinds are also possible.

The invention claimed is:

1. A method for measuring anesthesia parameters from the head of a patient, the method comprising the steps of:
   providing a base element of flexible material, the base element containing an array of at least three electrodes, an optical sensor for monitoring substances in the patient's tissues, and a connector connecting the at least three electrodes and the optical sensor to a patient monitor;
   placing the base element on the patient's head so that a first electrode in the array of electrodes is located between the eyebrows of the patient at about the centerline of the forehead;
   placing the base element on the patient's head such that second and third electrodes in the array of electrodes are positioned just posterior to the lower part of the pinna and just anterior to the tragus respectively;
   utilizing the second and third electrodes in the array of electrodes to stimulate a facial nerve and measure neuro muscular transmission;
   using at least the first electrode in the array of electrodes to measure electroencephalography and muscle activity; and
   using the optical sensor to measure substances in the patient's tissues.

2. The method of claim 1 comprising the steps of:
   placing the base element on the patient's head such that a fourth electrode of the array of electrodes is located on the temple area between the corner of the eye and the hairline, a fifth electrode of the array of electrodes is positioned above the eye and at the same vertical level as the first electrode in the array of electrodes, which is located between the eyebrows of the patient at the center of the forehead, about 4 cm above the nose, and a sixth electrode of the array of electrodes is positioned below the eye for enhancing encephalography and muscle activity measurement; and
   using the first, fourth and fifth electrodes to measure encephalography and muscle activity.

3. The method of claim 2 comprising the step of: using at least two of the first, fourth, fifth and sixth electrodes to measure neuro muscular transmission.

4. The method of claim 2 comprising the steps of:
   placing the base element on the patient's head such that a fourth alternative electrode in the array of electrodes is located on one of locations F3 and F4 of the International 10-20 system, a first electrode in the array of electrodes is located between the eyebrows of the patient at the center of the forehead, about 4 cm above the nose and a the sixth electrode is adapted for location below the eye for enhancing muscle activity measurement; and
   using the first and fourth alternative electrodes and the sixth electrode in the array of electrodes to measure encephalography and muscle activity.

5. The method of claim 1 wherein the optical sensor is positioned on the forehead of the patient when the base element is placed on the head of the patient.

6. The method of claim 1 wherein the optical sensor is positioned on the root of the nose of the patient when the base element is placed on the head of the patient.

7. The method of claim 1 wherein the optical sensor is positioned on the ear of the patient when the base element is placed on the head of the patient.

8. The method of claim 1 wherein the optical sensor is an SpO2 sensor.

9. A method for measuring anesthesia parameters from the head of a patient, the method comprising the steps of:
   providing a base element of flexible material, the base element containing an array of at least three electrodes, an optical sensor for monitoring substances in the patient's tissues, a mechanical neuro muscular transmission sensor, and a connector connecting the at least three electrodes, the optical sensor, and the mechanical neuro muscular transmission sensor to a patient monitor;
   placing the base element on the patient's head so that a first electrode in the array of electrodes is located between the eyebrows of the patient at about the centerline of the forehead;
   placing base element on the patient's head such that second and third electrodes in the array of electrodes are positioned just posterior to the lower part of the pinna and just anterior to the tragus, respectively, to stimulate a facial nerve;
   utilizing the second and third electrodes in the array of electrodes to stimulate a facial nerve;
   using at least the first electrode in the array of electrodes to measure electroencephalography and muscle activity;
   using the optical sensor to measure substances in the patient's tissues; and
   using the mechanical neuro muscular transmission sensor to measure neuro muscular transmission.

10. The method of claim 9 comprising the steps of:
    placing the base element on the patient's head such that a fourth electrode of the array of electrodes is located on the temple area between the corner of the eye and the hairline, a fifth electrode of the array of electrodes is positioned above the eye and at the same vertical level as the first electrode in the array of electrodes, which is located between the eyebrows of the patient at the center of the forehead, about 4 cm above the nose, and a sixth electrode of the array of electrodes is positioned below the eye for enhancing encephalography and muscle activity measurement; and
    using the first, fourth and fifth electrodes to measure encephalography and muscle activity.

11. The method of claim 9 wherein the mechanical neuro muscular transmission sensor is a piezoelectric sensor and comprising the steps of:
    placing the base element on the patient's head such that the neuro muscular transmission sensor is located over one of the procerus, frontalis, corrugator or orbicularis muscle or a combination of these; and
    using the mechanical neuro muscular transmission (NMT) sensor to record muscle response to NMT stimulus.

12. The method of claim 10 comprising the steps of:
placing the base element on the patient's head such that a fourth alternative electrode in the array of electrodes is located on one of locations F3 and F4 of the International 10-20 system, the first electrode in the array of electrodes is located between the eyebrows of the patient at the center of the forehead, about 4 cm above the nose and a the sixth electrode is adapted for location below the eye for enhancing muscle activity measurement; and
using the fourth alternative and the sixth electrodes in the array of electrodes to measure encephalography and muscle activity.

13. The method of claim 12 wherein the mechanical neuro muscular transmission sensor is a piezoelectric sensor and comprising the steps of:
placing the base element on the patient's head such that the neuro muscular transmission sensor is located over one of the procerus, frontalis, corrugator or orbicularis muscle or a combination of these; and
using the mechanical neuro muscular transmission (NMT) sensor to record muscle response to NMT stimulus.

14. The method of claim 9 wherein the optical sensor is positioned on the forehead of the patient when the base element is positioned on the head of the patient.

15. The method of claim 9 wherein the optical sensor is positioned on the root of the nose of the patient when the base element is positioned on the head of the patient.

16. The method of claim 9 wherein the optical sensor is positioned on the ear of the patient when the base element is positioned on the head of the patient.

17. The method of claim 9 wherein the optical sensor is an SpO2 sensor.

* * * * *